United States Patent [19]

Steele et al.

[11] 4,017,429

[45] Apr. 12, 1977

[54] PREPARATION OF 2-HYDROXYALKYL ESTERS

[75] Inventors: Roger B. Steele, Fair Oaks; Arthur Katzakian, Jr., Sacramento, both of Calif.

[73] Assignee: Aerojet-General Corporation, El Monte, Calif.

[22] Filed: Jan. 14, 1975

[21] Appl. No.: 540,776

Related U.S. Application Data

[60] Division of Ser. No. 389,079, Aug. 17, 1973, abandoned, which is a continuation-in-part of Ser. No. 4,056, Jan. 19, 1970, Pat. No. 3,968,135.

[52] U.S. Cl. .......................... 260/2 EP; 260/486 B; 260/488 F; 260/485 G; 260/468 R; 260/475 P; 260/326 A; 260/410.6
[51] Int. Cl.² .......................................... C08F 2/00
[58] Field of Search .......... 260/468 R, 414 X, 2 EP

[56] References Cited

UNITED STATES PATENTS

| | | | |
|---|---|---|---|
| 3,379,709 | 4/1968 | Louden | 260/414 X |
| 3,530,154 | 9/1970 | Stein et al. | 260/468 R |

FOREIGN PATENTS OR APPLICATIONS

| | | |
|---|---|---|
| 715,201 | 4/1968 | Belgium |

OTHER PUBLICATIONS

Wagner & Zook, "Synthetic Org. Chemistry," Wiley & Sons, New York, 1953, pp. 486–487.

*Primary Examiner*—Lewis Gotts
*Assistant Examiner*—Cary Owens
*Attorney, Agent, or Firm*—Marvin E. Jacobs

[57] ABSTRACT

This patent describes the catalytic promotion of the reaction of oxirane-containing compounds with carboxylic acid compounds at high, ambient, and low temperature. Specifically, this patent describes the method of reacting oxirane-containing compounds with carboxyl-containing compounds, preferably at temperatures at or around ambient, in the presence of active chromium III tricarboxylate salts which have unoccupied coordination sites. More specifically this patent describes the preparation of catalytically active chromium III-tricarboxylates from normally catalytically inactive chromium III tri-carboxylate hydrates. These compounds are powerful catalysts for the reactions of oxirane compounds with both organic carboxylic acids and cyclic primary imides.

15 Claims, No Drawings

PREPARATION OF 2-HYDROXYALKYL ESTERS

This application is a division of Ser. No. 389,079, filed Aug. 17, 1973, now abandoned, which in turn is a continuation in part of our co-pending application Ser. No. 4,056, filed Jan. 19, 1970, now U.S. Pat. No. 3,968,135, issued Sept. 14, 1976.

BACKGROUND OF THE INVENTION

Chrominum salts are known in which the oxidation state of chromium varies between one annd six. Extensive investigation has shown, however, that chromium III is the most stable and important oxidation state of the element. An important characteristic of the chromium III ion is that it has six coordination sites arranged in an octahedral configuration about the central ion. The coordination sites of chromium III account for the existence of stable complex ions such as the hexaaquochromium ion $Cr(H_2O)_6^{+++}$ and the hexaminochromium ion $Cr(NH_3)_6^{+++}$. In both of the above examples the water and ammonia, commonly called ligands (L), occupy the six coordination sites of chromium III and are arranged in an octahedral configuration about the central chromium III ion.

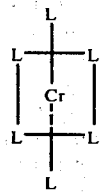

Ligands may be electrically neutral, as in the cases of water and ammonia, or negatively charged as in the case of the cyanide ion which gives rise to the negatively charged hexacyanochromium ion $Cr(CN)_6^{-3}$.

Further, chelating agents, such as the acetylacetonate anion, form exceedingly stable chromium chelates in which all of the chromium III coordination sites are occupied.

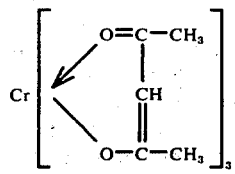

The removal of the above-mentioned ligands from the chromium III ion or the displacement of these ligands by other ligands is an extremely difficult and slow process. It is largely because of this kinetic inertness that so many complex chromium III species can be isolated and that they persist for relatively long periods of time in solution, even under conditions where they are thermodynamically quite unstable. Thus, the normally occurring form of chromium III compounds is the fully coordinated state. The kinetic stability of its widely found complex coordination compounds sets the chromium III ion apart from most other trivalent transition metal ions. We have found that the commonly occurring fully coordinated chromium III carboxylates are poor catalysts for carboxylic acid-oxirane reactions. Quite surprisingly, however, we have found that Chromium III compounds wherein coordination sites are readily available for coordination (complexing) by either charged or neutral ligands act as superior catalysts for such reactions and also for the acid-imide reaction.

SUMMARY OF THE INVENTION

Briefly, the present invention comprehends the method of reacting oxirane-containing compounds with carboxyl-containing compounds, preferably at temperatures at or around ambient, in the presence of active chromium III tricarboxylate salts which have available coordination sites. The invention also contemplates the process for preparing a catalyst for the acid-oxirane reaction and which is preferential thereto in the presence of ions which could interfere in other ways. The process comprises subjecting a chromium III tricarboxylate which has no readily available coordination sites to an excess of a carboxylic acid at temperatures in excess of 200° C to form the active chromium III tricarboxylate salt.

Henceforth, the term "active chromium III tricarboxylate salts" will be used to mean those chromium III salts having readily available coordination sites that can interact with charge bearing or neutral ligands of the type described earlier.

A prime object of the present invention is to provide a novel chromium catalyst for use in the reaction or oxirane moieties with carboxylic acid moieties.

Another object of the invention is to provide a novel chromium catalyst for use in the low temperature curing of oxirane containing compounds, and for a process for the production of the catalyst.

Another object of our present invention is to provide a novel process for the production of hydroxy alkyl esters at temperatures of about ambient temperature or less.

Still another object of the present invention is to provide a method of reacting poly epoxides with carboxylic acids at low temperatures.

A still further object is to provide a technique for the production of polycarboxylic acid-oxirane reaction products.

Yet another object is to provide a process for the reaction of polyfunctional polymeric epoxides with polyfunctional polymeric carboxylic acids.

These and other objects and advantages of this invention will be apparent from the detailed description which follows.

While not bound by any theory, it is believed that the catalysis of the acid-epoxy reaction by $Cr(OCOR)_3$ is based on the transient occupation of the available chromium III coordination sites by either an epoxide and/or a carboxylic acid molecule. This unique activated complex places the epoxide and the carboxylic acid in the proper geometric and energetic environment for reaction to occur. The catalyst is regenerated and thus is able to participate in further reactions. A typical reaction wherein both the epoxide and acid are coordinated to the chromium is shown below.

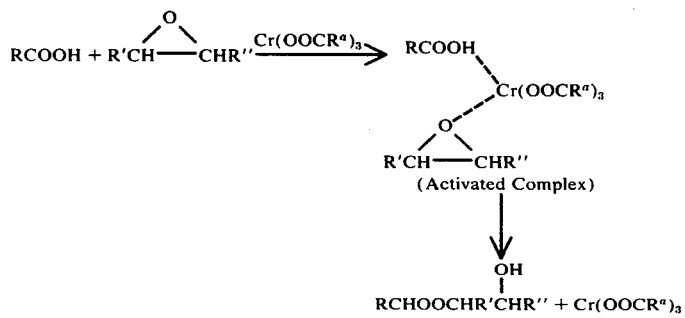

$$RCHOOCHR'CHR'' + Cr(OOCR^a)_3$$

where $R^a$ is aliphatic, aromatic, cyclo aliphatic, aralkyl, alkaryl, of from 1 to about 18 carbon atoms, as well as their containing imide, epoxy or acid non-reactable substituents such as halogens, cyano, ether, ester and amide. R, R' and R'' are the same or different hydrocarbon group. These active chromium III tricarboxylate salts fulfill three prerequisites for effective catalysis of the acid-epoxy reaction: (a) solubility in the reaction media, (b) coordination sites available for catalysis, and (c) the capability of forming kinetically stable coordination complexes so that reagent residence times on the chromium III ion are sufficient to permit reaction to occur. Generally the active chromium III salt will be in the carboxylate form, wherein $R^a$ is a hydrocarbon group. However, $R^a$ may be partially substituted as above to impart desirable specific physical properties to the catalyst for certain applications. These properties include improved solubility, better catalyst stability, lower melting point and the like.

While as stated, it appears that only one coordination site need be utilized for reactant coordination to achieve catalytic activity for the active chromium compound, it is seen that the more sites made available for such coordination the greater the catalytic activity of the compound as will be set forth in detail elsewhere, the sites are rendered available for coordination by deaquation, namely the removal of coordinated water.

The preferred chromium III tricarboxylate salts are those in which three of the six coordination sites on chromium III are unoccupied and are thus available to participate in catalysis. Here, three chromium III coordination sites are occupied by the carboxylate anions to produce a neutral molecule; the remaining three sites being unoccupied. The R side chain group of the carboxylate anions may be adjusted in order to effect the necessary solubility in various reaction media necessary for efficient catalysis. The structure of a typical chromium III tricarboxylate salt processing three unoccupied coordination sites may be envisioned as follows:

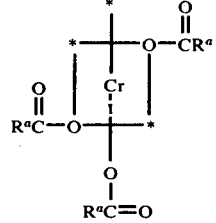

\* = Available coordination sites.

Each $R^a$ may be as defined above.

The advantages of the present invention have been found to be obtained using any soluble trivalent chromium III tricarboxylate salt containing unoccupied coordination sites. In this form, the compounds are said to be in the activated state. Typical compounds which when activated find use in this invention, include but are not limited to, trivalent chromium hexanoate, trivalent chromium pentanoate, trivalent chromium butyrate, trivalent chromium 2 ethyl-hexanoate, trivalent chromium decanoate, trivalent chromium oleate, trivalent chromium stearate, trivalent chromium toluate, trivalent chromium cresylate, trivalent chromium benzoate, trivalent chromium alkylbenzoates, trivalent chromium alkoxybenzoates, trivalent chromium naphthanates and trivalent chromium alkoxides. Generally, although not necessarily, the dehydrated trivalent chromium catalysts of our invention contain in toto from about 6 to about 60 carbon atoms. We have found that these catalysts are at least somewhat soluble in the reaction system. This solubility is essential to the effectiveness of the catalyst. However, the exact degree of solubility is not critical.

The catalysts of the present invention may be utilized in any of several reactions between oxirane moieties and carboxylic acid moieties.

The catalysts can be used for any of the below set forth reactions, to aid in the formation of any of the polymers, monomers, and capped large chain molecules.

1. $$R-A_c + R'O_x \xrightarrow[\text{(Active)}]{Cr^{III}} R-E_x(H_y)R'$$
   (Green)

2. $$2R-A_c + R'-O_x-L-O_x-R' \xrightarrow[\text{(Active)}]{Cr^{III}} R-E_x(H_y)-L-(H_y)E_x-R$$
   (Green)  $\quad\quad\quad$ R' $\quad\quad\quad$ R'

3. $$R-(A_c)-L-(A_c)-R + 2R'-O_x \xrightarrow[\text{(Active)}]{Cr^{III}} R'-(H_y)E_x-L-E_x(H_y)-R'$$
   (Green)  $\quad\quad\quad$ R $\quad\quad\quad$ R -continued 4.  $R(A_c)-L-[(A_c)-L-]_m(A_c)-R + (m+2)R'O_x$

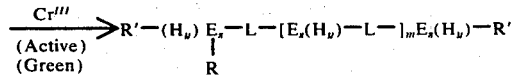

or

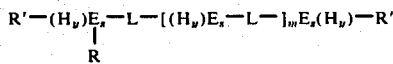

5.  $(m+2) R-A_c + R'-O_x-LO_x-L)_mO_x-R'$

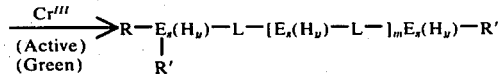

or

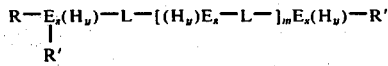

6.  $R-(A_c)-L-[(A_c)-L-]_m(A_c)-R + R'-O_x-L-[O_x-L-)_mO_x-R'$

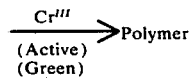

$A_c$ is a carboxylic acid moiety
$O_x$ is an oxirane moiety
$E_s$ is an ester moiety
$H_y$ is an hydroxyl moiety
L is a multivalent organic linking group which may be any of alkyl, aryl, aralkyl, alkaryl, alkylene, or any of the above with non interfering substituents such as fluoro, chloro, bromo, iodo, cyano, keto, ester, ether, etc.
R is a proton or an organic radical of 1-20 carbon atoms which may be any of alkyl, aryl, aralkyl, alkaryl, alkylene, or any of the above hydro-carbon m moieties substituted with non-interfering groups as described in the definition for —L—. All R's may be the same or different.
R' is defined the same as R
Wherein any $A_c$ moiety, and any $H_y$ moiety may be relatively positioned as a terminal or pendant group; and any $O_x$ moiety may be relatively positioned as either a terminal group or a divalent internal group positioned along the molecular backbone. $m = o$ or a positive integer.

DESCRIPTION OF PREFERRED EMBODIMENTS

Chromium III salts in which the coordination sites are occupied by water, are referred to as "aquated" chromium III compounds. The aquated compounds are those that are generally available in the market place as chromium III salts. Aquated chromium III coordination complexes differ from most simple metal salt hydrates in that dehydration of simple metal salt hydrates may be accomplished by storage over dehydrating agents such as sulfuric acid. Alternatively, mild heating (ca. 100° C) is routinely employed to dehydrate common metal salt hydrates such as calcium and magnesium sulfate hydrates. On the other hand, aquated chromium III carboxylates can be heated to high temperatures with only moderate loss of water. However, it should be understood that the mere driving off of a portion of retained water, is not sufficient to prepare our novel catalysts.

The novel catalysts are prepared by the dehydration of the chromium III commercial carboxylate salts in the presence of an acidic deaquation aid during this dehydration a chemical structure rearrangement takes place.

When only heat is applied, the normally violet carboxylate salts will either remain violet or change to a blue cast. This change indicates that approximately 2 of the 3 water molecules present have been removed. Continued heating does not remove the third molecule of water, the third water molecule is only readily removed when performed in the presence of about 0.7 mole percent acidic material such as organic carboxylic acids, as for instance additional acid corresponding to the carboxylate anion of the chromium compound or a different acid such as a para toluene sulfonic acid. When the final water molecule is removed, a product results having the following characteristics.

(1) It is emerald green in color, (2) slightly soluble in hexane, but freely soluble in acetone, (3) it melts slightly above room temperature, (4) it does not have a water absorption peak at 2755 mm in the near infrared, (5) and it has a carboxylate carbonyl absorption at 1615 $cm^{-1}$ in the infra-red region which is shifted from that for the hydrated form.

These properties are in marked contrast to the commercial hydrated chromium III carboxylates. The hydrated form on the other is readily soluble in hexane, and completely insoluble in acetone, does not show any tendency to melt up to 300° C., it is violet in color, it has a strong absorption at 2755 in the near infrared, and it has a broad characteristic carboxylate carbonyl absorption at 1540 $cm^{-1}$ in the infra-red region.

Previously we have mentioned that the third water molecule can be removed from a typical salt such as chromium III tri 2-ethyl hexanoate by the use of an acidic deaquation aid subsequent to the removal of the first two water molecules. If, however, the acidic aid is added at the commencement of the heating cycle, then dehydration and rearrangement to the catalytic (active form) of the chromium compound can occur simultaneously. In this manner a random statistical mixture of hydrated, non-hydrated and partially dehydrated salt is formed. The fully dehydrated portion will rearrange to the catalytically active charge. The color is seen to vary from the original blue-violet through blue to green. The catalytic capability is proportional to the amount of green material present. The ratio of active to inactive catalyst in this mixture can be measured spectrophotometrically by determining the ratio of the carbonyl absorption at 1615 cm$^{-1}$ to the carbonyl absorption at 1540 cm$^{-1}$.

not cause complete coordination. For example, if the carboxylate anion is replaced by the acetylacetonate anion the resulting chromium III acetylacetonate is catalytically inactive under our test conditions. The reason for this is that the acetylacetonate groups effectively occupy all of the chromium III coordination sites. The same inactivity occurs if the active chromium III tricarboxylate is contacted with a non-charged specie such as ethylene diamine to form the ethylene diamine complex of the salt.

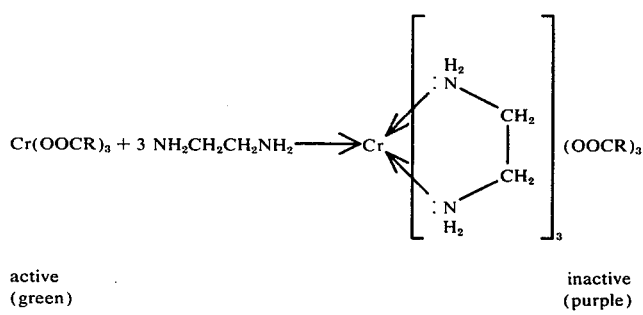

active (green)

inactive (purple)

Once the necessary coordination sites on chromium III have been freed for catalyst participation, care must be taken to insure catalyst activity during the reaction. Inert solvents such as benzene, toluene, methylisobutyl ketone, etc., are acceptable. Electron donating solvents such as methanol, ethanol, dimethylformamide, dioxane and tetrahydrofuran, however, were found to retard catalysis at certain temperatures in such instances. These electron donating solvent molecules tend to congregate around the chromium III coordination sites and block the transient residence of the acid-epoxy reagents on these sites and thus prevent reaction catalysis.

In general, the inactive (hydrated) chromium III tricarboxylate salts are prepared by the reaction of an aquated inorganic chromium III salt such as aquated chromium nitrate with three moles of sodium carboxylate.

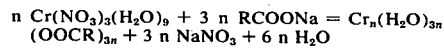

The chromium III salt obtained by this method is catalytically inactive since the six chromium III coordination sites are occupied by the water. In order to produce the active catalyst, the aquated form must be subjected to a high temperature, acid catalyzed process in which the coordination sites are freed of water as recited above.

Active Catalyst

In the above two equations, R is a monovalent organic radical such as alkyl, aryl, alkaryl or aralkyl, and preferably contains from 1 to about 20 carbon atoms.

While we have previously defined the term active chromium III, by the term "inactive" as a modifier for salt, chromium III, etc., we mean that the level of catalytic activity is up to and no greater than that of other commonly used metal-organo salt catalysts such as stannous octoate, and iron oleate, and in many instances non-catalytic at all.

The anion (negatively charged) portion of the catalyst is also critical to its activity in the sense that it may It is seen that while this application is directed to the reaction of oxiranes with carboxylic acids, both monomeric and polymeric that the catalysts will aid in the reaction of axiranes with other compounds which contain labile hydrogens, such as organic cyclic primary imides both monomeric and polymeric, monofunctional and polyfunctional.

The following examples are presented solely to illustrate the invention and accordingly should not be regarded as limiting in any way. In the examples, the parts and percentages are by weight unless otherwise indicated.

EXAMPLE I

Preparation of Non-Catalytic, Aquated Chromium III Tri-2-Ethylexanoate

A solution of 120 g (3.0 moles) of sodium hydroxide was dissolved in 500 ml of distilled water. 2-Ethylhexanoic acid (475 g, 3.3 moles) was added with stirring to form sodium 2-ethylhexanoate. In a separate container, 200 g (0.5 mole) of chromium nitrate nonahydrate was dissolved in 500 ml of distilled water. The chromium nitrate solution was slowly added to the sodium 2-ethylhexanoate solution with good stirring. When the addition was complete, 500 ml of hexane were added and stirring was continued for 10 minutes. The layers were separated and the hexane layer containing the aquated chromium III tri-2-ethylhexanoate was washed with dilute sodium hydroxide solution, water, dilute sodium carbonate solution and finally with distilled water. The hexane solution was then dried over anhydrous magnesium sulfate. Most of the hexane was removed under reduced pressure and the resulting concentrate was slowly added to 500 ml of acetone. The resulting blue granular solid was filtered and air dried to yield 130 g (54%) of aquated chromium tri-2-ethylhexanoate. Molecular weight determination indicated that the compound is polymeric in nature, probably due to the oxygen bridging of chromium atoms.

Anal. Calcd for $C_{24}H_{51}O_9Cr$: C, 53.8; H, 9.6; Cr, 9.7. Found: C, 53.2; H, 8.7; Cr, 9.4.

Azeotropic data indicated three molecules of water per chromium atom.

The discrepancy in the hydrogen analysis is believed to be caused by chromium interference.

EXAMPLE IIa

Preparation of Catalytically Active Chromium Tri-2-Ethylhexanoate

A stock solution of 5.0 g. of aquated chromium tri-2-ethylhexanoate and 2.5 g of 2-ethylhexanoic acid in chloroform was prepared. Ten-ml aliquots of this solution were transferred to each of ten 50-ml volumetric flasks and placed in a 140° oven for 0 (control), 0.5, 1.5, 3 and 6 hours. After each time interval two of the flasks were removed from the oven. One was diluted to the mark with carbon tetrachloride and the conversion from aquated to active chromium tri-2-ethylhexanoate was determined by measuring the absorption intensity of the solution at 275 millimicrons. It was determined that fully aquated chromium tri-2-ethylhexanoate absorbs strongly at 275, millimicrons while the active deaquated chromium compound does not absorb at this wavelength. The conversion from catalytically inactive fully coordinated aquo chromium tri-2-ethylhexanoate to the active form is illustrated in Table 1.

TABLE I

| CONVERSION FROM INACTIVE TO ACTIVE CHROMIUM III TRI-2-ETHYLHEXANOATE | | |
|---|---|---|
| Time at 140° C, Hour | % Deaquated Chromium** | % Free Coordination Sites |
| 0 | 0 | 0 |
| 0.5 | 6.9 | 6.9 |
| 1.5 | 14.0 | 14.0 |
| 3.0 | 33.0 | 33.0 |
| 6.0 | 44.0 | 44.0 |
| * | 90.0 | 90.0 |

*In order to free the desired large percentage of the coordination sites on chromium III, additional 2-ethylhexanoic acid was added and the solution was heated at 200° C.

To the other 50-ml volumetric flasks removed from the 140° oven at the above time intervals was added 30 ml of a solution containing 144 g (2.0 moles) of 1.2-butylene oxide and 14.4 g (0.1 mole) of 2-ethylhexanoic acid diluted with toluene to a volume of 500 ml. The flasks were then diluted to the mark with toluene. This operation provided solutions for the kinetic study having the following reagent concentrations:
2-ethylhexanoic acid — 0.12 molar
1,2-butylene oxide — 2.40 molar
chromium compound — 0.019 molar A control sample containing no chromium compound was also prepared. 5-ml aliquots of these solutions were quenched into 50-mil portions of methanol and the unreacted acid determined by titration with base. The catalytic activity of the chromium tri-2-ethylhexanoate in various stages of aquation is summarized in Table II.

EXAMPLE IIB

When the 2-ethylhexanoic acid was replaced by oleic acid in the amount of 928 grams, utilizing a substantially similar procedure,, as in Example I, aquated chromium oleate was prepared, the conversion to the active form was carried out by heating at elevated temperatures the aquated form of the compound in a distilling flask with a Dean Stark tube connected thereto for removal of the moisture. During the course of the heating excess of oleic acid is added as a deaquation aid.

Table II

CATALYTIC ACTIVITY OF CHROMIUM TRI-2-ETHYLHEXANOATE IN VARIOUS STAGES OF AQUATION AT 22° C
REACTION OF 2-ETHYLHEXANOIC ACID WITH 1,2-BUTYLENE OXIDE

| Reaction Time, Hour | 2-Ethylhexanoic Acid Utilized, % | | | | | | |
|---|---|---|---|---|---|---|---|
| | No Chromium | Fully Aquated | 93% Aquated | 86% Aquated | 77% Aquated | 56% Aquated | 10% Aquated |
| 0.50 | 0 | 0 | 0 | 0 | 0 | 0 | 0 |
| 1.00 | 0 | 0 | 0.2 | 3.0 | 6.0 | 22 | 100 |
| 2.00 | 0 | 0 | 0.5 | 6.4 | 13.0 | 58 | 100 |
| 4.00 | 0 | 0 | 0.8 | 12.0 | 20.0 | 96 | 100 |
| 8.00 | 0.1 | 1.0 | 2.0 | 28.0 | 50.0 | 100 | 100 |
| 12.00 | 0.1 | 1.2 | 3.0 | 47.0 | 73.0 | 100 | 100 |
| 24.00 | 0.5 | 3.0 | 6.0 | 100.0 | 100.0 | 100 | 100 |
| 48.00 | 1.0 | 5.5 | 15.0 | 100.0 | 100.0 | 100 | 100 |
| 72.00 | 1.4 | 10.6 | 12.8 | 100.0 | 100.0 | 100 | 100 |
| — | | $\frac{54}{536} = 10.03$ | $\frac{52}{534} = 9.74\%$ | $\frac{46.5}{5285} = 8.8\%$ | $\frac{41.6}{5236} = 7.95\%$ | $\frac{30.2}{512.2} = 5.9\%$ | $\frac{5.4}{487.4} = 1.11\%$ |

Wt% H₂O based upon total molecular weight.
In the above table, fully aquated means that all three water molecules are still bonded to each chromium nucleus. The percentage of aquation recited actually constitutes that percent of 100% aquation which is the amount of water equal to three bonded water molecules and such percent of Wt% H₂O based upon total molecular weigl As shown in Table 2, the active chromium III salt having 90% open coordination sites caused the acid-epoxy reaction to be 100% complete in 1 hour at 22° C. The fully aquated chromium salt, on the other hand, caused only 10.6% reaction to occur in 72 hours, only slightly faster than the uncatalyzed reaction. More sophisticated kinetic calculations indicate that the acid-epoxy reaction proceeds approximately 10,000 times faster at 23° C when catalyzed with 1% active chromium tri-2-ethylhexanoate than in the uncatalyzed reaction. The data also show that the active chromium tri-2-ethylhexanoate having unoccupied coordination sites is approximately 1000 times more effective than the fully aquated chromium III salt. Superior catalytic activity is not achieved until nearly all of the occupied coordination sites on chromium III have been freed for catalyst participation.

The invention is applicable to any monofunctional oxirane oxygen compound including ethylene oxide, 1,2-propylene oxide, 1,2-butylene oxide, 2,3-butylene oxide, 1,2-epoxyhexane, cyclohexene oxide, styrene oxide and others of the

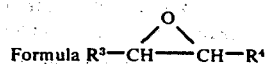

Formula $R^3-CH\underset{\diagdown O \diagup}{\phantom{X}}CH-R^4$ wherein $R^3$ and $R^4$ are hydrogen or alkyl, total carbon content being from 1 to 20 carbon atoms.

The polyfunctional epoxide materials for use in the invention include organic materials having a plurality of reactive 1,2-epoxy groups. The mono and polyfunctional epoxide materials can be saturated or unsaturated, aliphatic, cycloaliphatic, aromatic or heterocyclic, and they may be be substituted if desired with other substituents besides the epoxy groups, e.g. hydroxyl groups, ether radicals, halogen atoms, and the like. Such oxiranes having a plurality of epoxy groups utilizeable include 1,2,3,4-diepoxy butane, 1,2,5,6-diepoxy hexane, diepoxide of divinyl benzene, and the like. The invention is particularly adapted to the reaction of any epoxyalkanes or epoxycycloalkanes, typically containing from 2 to about 20 carbon atoms, with organic carboxylic acids.

It is within the scope of this invention to utilize as oxirane constituents not only the di addition products of such phenols as Bisphenol A with epichlorohydrin and the like, but also the higher molecular weight diepoxides of polybisphenol compounds, as well as the polyepoxy novolac compounds wherein the molecular weights vary statistically.

As indicated previously the catalyst of this invention can be utilized in the reaction of epoxy materials which are themselves polymeric with carboxylic acids. If the acid component has monoacid functionality, then hydroxyalkyl esters are formed on the epoxy resin backbone. If however multi acid functionality commpounds are used the compounds formed are larger block polymers linked by monomeric units. If however the multifunctional acids are themselves polymeric, a block copolymer would be formed.

The epoxy resins which may be used in the practice of this invention include any of those materials familar to those skilled in the art. Typical epoxy resins suitable in the practice of the present invention are those disclosed in U.S. Pat. Nos. 2,500,600 and 2,324,483, the disclosures of which are expressly incorporated herein by reference. While not limited thereto, the epoxy resins of th present invention normally have epoxy equivalent weight values of from about 100 up to 4000 or higher. The more common types of epoxy resins are the reaction products of epichlorhydrin and 2,2-di(p-hydroxyphenyl) propane, the glycidyl ether of mononuclear di- and trihydroxy phenols (resorcinol, hydroquinone, pyrocatechol, saligenin and phloroglucinol), the glycidyl ether of other polyhydroxyl phenols (Bisphenol F, trihydroxyldiphenyl dimethyl methane, 4,4'-dihydroxy biphenyl, tetrakis (hydroxyphenyl) ethane, longchain bisphenols, dihydroxy diphenyl sulfone, and Novolacs), the glycidyl ethers of polyalcohols (ethylene glycol, 1,4-butanediol, glycerol, erythritol, and polyglycols), and the epoxylated cyclic and straight chain olefins (vinyl cyclohexene, dicyclohexene carboxylate, and polybutadienes). These and many other epoxy resins are available plasticizer commercially for example, under the trade name "Epon Resins" from the Shell Chemicals Company, "Araldrite Resins" from the Ciba Company, "DER Resins" from the Dow Chemical Company and "Unox Epoxides" from Union Carbide Chemicals Company.

Carboxylic acids utilizeable herein may be monofunctional as well as di and polyfunctional. They may also be saturated or unsaturated aliphatic, aromatic, heterocyclic, monomeric and polymeric in nature. They may also contain non-interfering groups other than carboxylic acid as substituents on the organic backbone. Typical of the monofunctional acids are acetic, formic, 2-ethyl hexanoic, octanoic, salicyclic, dodecanoic, oleic, 2-methoxy proprionic, toluic, ascorbic, linoleic, linolenic, acrylic, methacrylic, benzoic, naphthoic, chloroacetic, lactic, ricinoleic, stearic, benzylic, butyric, cyclohexane, carboxylic, picolinic and furane carboxylic, acids.

Polyfunctional monomeric acids utilizeable include citric, citroconic, maleic, itoaconic, oxalic acid, malonic acid, succinic acid, glutaric acid, adipic acid, pimelic acid, azelaic acid, sebacic acid, brassylic acid, trimellitic acid, trimesic acid, phthalic acid, isophthalic acid, o, m and p, dicarboxy benzophenones.

Mention should also be made of polyfunctional polymeric acids, these include carboxy functional polyesters, carboxyterminated polyolefins, e.g. polybutadiene, carboxy terminated polyethers such as the succinic acid half ester of polyether glycols; dimerized and trimerized fatty acids.

In the practice of the invention, the activated trivalent chromium compound is used in an effective catalytic amount, of from about 0.1 to about 10% based on the total weight of the three key components, namely the oxirane, acid, and catalyst. Thus if a 1 percent level is desired, 99 grams of a mixture of the oxirane and acid components would be utilized with 1 gram of catalyst.

If other miscible or soluble ingredients are added to the system the catalyst level must be based upon the total weight in grams of the solution phase. Thus if a plasticizer is added to the 99 grams of reactants, and is present in the weight of 49.5 grams, the catalyst level need be set at 1.5 grams to maintain a catalyst concentration of 1% if it is desired to maintain comparable reaction rates to the above reaction without plasticizer.

If inert insoluble materials such as carbon black, silica gel, $CaCO_3$ and the like are added to the system, their weight is not to be taken into consideration in calculating the catalyst level.

The following examples relate to the preparation of monomeric compositions in the presence of the catalyst of this invention.

EXAMPLE III

Preparation of Hydroxypropyl Acrylate

The reaction of 5.0 moles acrylic acid with 5.5 moles propylene oxide under pressure in the presence of the catalyst of Ex. II (0.28% by weight of total system) at 70°–75° C gave both B-hydroxy alkyl ester isomers. The material was, isolated by wiped-film distillation (b.p. 55° to 60° C at 0.02 to 0.05 mm), in 86.7% yield and 99.3% purity based on titration with alcoholic potassium hydroxide, and on gas chromatography analysis for unreacted acid.

EXAMPLE IV

Preparation of 2-Hydroxyethyl Acetate

The 2-hydroxylethyl ester of acetic acid was prepared in methyl isobutyl ketone by allowing 5.0 moles acetic acid and 5.5 moles of ethylene oxide to react in the presence of 0.28% of the catalyst of Example II (based on weight of total system) under pressure at 150°–160° C for 2 hours. The acid was quantitively converted as determined by titration with aqueous N/10 sodium hydroxide. Vacuum distillation of the crude ester gave a colorless product boiling at 64°–67° C at 2 mm pressure, having a refractive index of 1.4202 at 25° C.

EXAMPLE V

Preparation of Bis(2-Hydroxyethyl)Adipate

Adipic acid (36.5g, 0.25 mole) and the catalyst of Example II (0.4g) in methyl isobutyl ketone (250 ml) were heated at 160° C and subsequently ethylene oxide (24.23g, 0.55 mole) was added; the temperature was kept at 160° C. After 60 minutes, the pressure dropped from 103 psi to 57 psi. After solvent evaporation, the crude product (60.4g) was distilled under vacuum; a light yellow material (35.0g) was obtained boiling at 202°–203° C at 1 mm pressure in 60.0% yield, having a refractive index of 1.4619 at 25° C. The infrared spectrum was consistent with that expected for the ester (3450 cm$^{-1}$ (OH), 2970 cm$^{-1}$ (CH$_2$), 1730 cm$^{-1}$ (C=O), and 1180 cm$^{-1}$ (C—O)). Anal. Calcd. for C$_{10}$H$_{18}$O$_6$: C, 51.28; H, 7.69; O, 41.03, Found: C, 50.80; H, 7.76; Molecular weight by hydroxy number: Theory: 234. Found: 234.

EXAMPLE VI

Preparation of Bis(2-Hydroxyethyl)Azelate

The reaction of 0.25 moles azelaic acid with 0.55 moles ethylene oxide under pressure using methyl isobutyl ketone in the presence of the catalyst of Example II (0.15% by wt. of total system) at 153° C gave bis(2-hydroxyethyl)azelate in quantitative crude yield. The material was isolated as a grey-white solid melting at 46°–47° C from a n-butyl chloride-acetone mixture in 88.5% yield.

EXAMPLE VII

Preparation of Bis(2-Hydroxyethyl)Oxalate

The 2-hydroxyethyl ester of oxalic acid was prepared in the 1-liter autoclave using ethylene oxide and 0.1% of the catalyst of Example II (based on total weight of system) in methyl isobutyl ketone at 150°–170° C for 2hours. The conversion of acid was 76% of theory and vacuum distillation of the crude ester gave a product boiling at 194°–196° C at 8mm. The product was of high purity as established by hydroxyl number and elemental analysis.

Examples III to VII when repeated using activated forms of trivalent chromium butyrate, trivalent chromium oleate, and trivalent chromium toluate in lieu of the catalyst of Example II, give rise to similar results. Each of these catalysts is prepared and activated in the manner described in Example II, using the corresponding carboxylate as recited here.

EXAMPLE VIII

Preparation of Tris(2-Hydroxyethyl)Cyclohexanetricarboxylate

Cyclohexanetricarboxylic acid was allowe to react under pressure with ethylene oxide and 0.15% of the catalyst of Example II (based on the total wt. of system) in the presence of methyl isobutyl ketone at 150°–160° C for 2 hours. A viscous oil of good purity was obtained after charcoal treatment and evaporation of a methyl isobutyl ketone solution. The infrared spectra and elements analysis were consistent with the desired product.

EXAMPLE IX

Preparation of Tris(2-hydroxyethyl)Trimesate

Trimesic acid (1,3,5-benzene tricarboxylic acid) was converted to its tris-hydroxyethyl derivative using the catalyst of Example II at 1.0% by weight of reactants level. The trimesate ester gave an infrared scan consistent with the structure of the product and melted sharply at 145° C after purification. The reaction was carried out in methyl isobutyl ketone at room temperature for 44 hours, and gave an 89% conversion of the acid and an 87% recovery of the ester.

EXAMPLE X

Preparation of 2-Hydroxylethyl Acrylate

Acrylic acid (360g, 5.0 mole: inhibited with p-methoxy-phenol) in the presence of ethylene oxide (242g, 5.5 mole) and the catalyst of Example II (3.6, g 0.6% by weight of system) was heated in a 1-liter pressure autoclave at 52°–65° C for 50 minutes; during the reaction, the pressure dropped from 39 to 0 psia. The crude yield was 92% based on the converted acid as determined by titration of an aliquot with cold aqueous N/10 sodium hydroxide for unreacted acid. Distillation of the crude material gave a colorless product with a refractive index of 1.4495 at 23° C.

When the foregoing example is repeated using 1,2-propylene oxide and 1,2-butylene oxide, 2-hydroxypropyl acrylate and 2-hydroxybutyl acrylate, respectively, are obtained respectively.

EXAMPLE XI

Preparation of Bis(2-Hydroxyethyl)Sebacate

Sebacic acid (50.5g, 0.25 mole), the catalyst of Example II (0.5g), and methyl isobutyl ketone (250 ml) were charged to the autoclave and heated to 150° C. Ethylene oxide (24.23g, 0.55 mole) was introduced from a nitrogen-pressurized cylinder to the autoclave. The temperature rose to 160° C and the pressure increased from 25 psi to 100 psi. After 60 minutes at 160° C, the pressure dropped to 88 psi and the system was vented. The light yellow green reaction mixture was mixed with carbon black, heated to boiling, and filtered through a sintered-glass funnel containing some Al$_2$O$_3$. Upon cooling to −30° C, the precipitated material was filtered, washed with cold hexane, dried in a vacuum desiccator for 48 hours and weighed (31.0g). The product was isolated in 44.0% yield and melted at 47° C. The infrared bands at 3350 cm$^{-1}$ (OH), 2970 cm$^{-1}$ (CH$_2$) and 1730 cm$^{-1}$ (C=O) were characteristic of the expected ester. Anal. Calcd. for C$_{14}$H$_{26}$O$_6$: C, 57.93; H, 8.97; O, 33.10, Found: C, 58.00; H, 9.02. Molecular weight by hydroxyl number. Theory: 290. Found: 289.

EXAMPLE XII

Preparation of Bis(2-Hydroxyethyl)Terephthalate

Terephthalic acid (0.25 mole), the catalyst of Example II (0.5g), and methyl isobutyl ketone (250 ml) is charged to an autoclave and heated to about 150° C. A slight stoichiometric excess of ethylene oxide is added to the autoclave. A slight exotherm is observed. After about 1 hour, the reaction mixture is removed from the autoclave, cleaned, and filtered. Upon cooling, a good yield of bis(2-hydroxyethyl)terephthalate is obtained in the form of a precipitate.

EXAMPLE XIII

An epoxy resin system comprising about 12 parts Unox Epoxide 201, equivalent weight 156 (3,4-epoxy-6-methyl-cyclohexylmethyl 3,4-epoxy-6-methyl-cyclohexane carboxylate) and about 8 parts Empol 1040 is treated at about 50° C with about 2% by weight of the catalyst of Example II. The system cures in about 45 minutes. At 25° C, the system cures in about 10–12 hours.

The following example illustrates a capping reaction.

EXAMPLE XIV

One mole of ethylene oxide is reacted with about 0.5 moles of carboxy-terminated polybutadiene (available commercially under the tradename Butarez CTL) for about 4 hours in the presence of 1% of the catalyst of Example II. The reaction temperature is about 40° C. A hydroxyethyl diester of the carboxy-terminated polybutadiene is obtained.

In order to illustrate the difference between the active and non-active forms of the chromium carboxylate the following experiments were carried out.

EXAMPLE XV

Into two 100 ml round bottom flasks, each equipped with a reflux condenser was placed a solution of 1.0 g of anhydrous chromium 2-ethylhexanoate in 35 ml of MIBK in one flask and 1.2 g of non-active chromium compound in the other.

To these portions were added 28g (17 moles) of terephthalic acid followed by 17g (170 moles) of cyclohexene oxide. The resulting mixtures were refluxed for 5 min. At this time all of the acid with anhydrous catalyst had reacted and was in the solution. Filtration of the reaction mixture employhydrated chromium catalyst allowed recovery of 2.5g (90%) of unreacted terephthalic acid.

EXAMPLE XVI

Into two 125 ml Florence flasks was placed 1.0 g of non-active chromium octoate in the first and 1 gram of active chromium octoate in the other, both dissolved in 35 ml of toluene. To this solution has added 2.5g of 2-ethylhexanoic (17 mmol) acid followed by 17g of cyclohexene oxide (170 mmol). The progress of the reactions was followed by removing 2.0 ml samples and quenching in 50 ml of methanol and titrating with 0.1N methanolic KOH (phenophthalein end point).

|     | Non-Active Cr. ml base | Active Cr. ml base |
|-----|------------------------|--------------------|
| 0   | 7.0                    | 7.0                |
| 2.5 | 6.8                    | 3.4                |
| 7.0 | 6.4                    | 0.55               |
| 25  | 5.4                    | 0.30               |
| 50  | 4.7                    | 0.30               |

For the purposes of this application, the term octoate and 2-ethyl hexanoate are considered interchangeable.

The term COT is utilized to designate active chromium octoate.

The following examples serve to illustrate the fact that the catalyst of this invention is utilizable for the catalysis of the oxirane-imide reaction. It is to be seen that while the examples relate to monofunctional monomeric reactants, the reaction of polyfunctional materials is seen to be similarly catalyzed.

EXAMPLE XVII

Reaction of Tetrahydrophthalimide With 1,2-Propylene Oxide at 0° C in Acetone

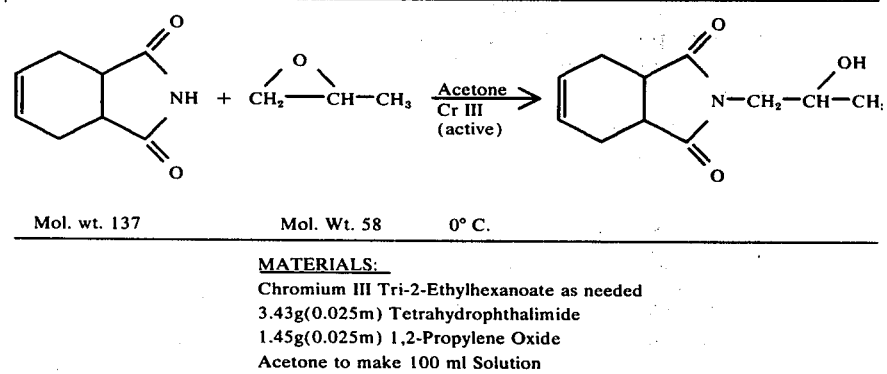

Mol. wt. 137   Mol. Wt. 58   0° C.

MATERIALS:
Chromium III Tri-2-Ethylhexanoate as needed
3.43g(0.025m) Tetrahydrophthalimide
1.45g(0.025m) 1,2-Propylene Oxide
Acetone to make 100 ml Solution

PROCEDURE:

Two solutions of the above composition were prepared having respectively 0 and 2% chromium III Tri-2-Ethylhexaneate. These solutions were prepared in 100 ml volumetric flasks which were kept at 0° C in an ice-water bath. Five ml aliquots were taken at various time intervals and titrated for unreacted imide with 0.25N alcoholic KOH using a pH titrimeter.

| 0% Chromium III Tri-2-Ethylhexanoate | | 2% Chromium III Tri-2-Ethylhexanote | |
|---|---|---|---|
| Elapsed Time, Min | % Imide Reacted | Elapsed Time, Min | % Imide Reacted |
| 0    | 0 | 0    | 0  |
| 50   | 0 | 40   | 9  |
| 110  | 0 | 100  | 50 |
| 155  | 0 | 145  | 59 |
| 215  | 0 | 205  | 66 |
| 275  | 0 | 265  | 69 |
| 1115 | 0 | 1105 | 85 |
| 1300 | 0 | 1290 | 86 |

The table above illustrates the catalytic activity of the active chromium III tri-2-ethylhexanoate, for a typical oxirane-primary cyclic imide reaction of 0° C.

The following examples illustrate the preparation of polymers using the noval catalyst of this invention.

EXAMPLE XVIII (Diacid With Triepoxide)

A stoichometric mixture of Emery 1025-94 acid (E.W. 1600), a polyester dicarboxylic acid, and EPON-X-801 (E.W. 109), 1,3-diepoxypropyl, 2-phenylglycidyl ether, was prepared with 3% active chromium III tri-2-ethylhexanoate.

The sample was split into two parts. One part was placed in a 75° C ovem where it cured to a tough, rubbery, greenish solid within fifteen minutes. The other part was left at room temperature where it also cured to a tough, rubbery, greenish solid within twenty hours.

EXAMPLE XIX (Triacid with Diepoxide)

This example illustrates the high catalytic activity of the activated chromium III tricarboxylate catalysts for the oxirane/carboxylic acid reaction at room temperature and well below, as well as the tremendous acceleration effect of added heat.

A stoichiometric mixture of trimer acid (E.W. 290) a triacid derived from the trimerization of fatty acids, and ERL-4421 (E.W. 136), 3,4-epoxy cyclohexylmethyl-(3,4-epoxy)cyclohexane carboxylate, was catalyzed with active chromium III tri-2-ethyl-hexanoate at three levels and cured at three temperatures. The catalyst levels, cure temperatures and mechanical properties are tabulated below:

Effect of catalyst level and cure temperature on the Mechanical Properties of Emery Trimer Acid & ERL-4221 Catalyzed with active chromium III-tri-2-ethyl hexanoate.

| Catalyst Level | 1% | 3% | 5% |
|---|---|---|---|
| Gel Time at 25° C | — | 129 min | 57 min |
| Cure Temp, ° C | 60° C | 25° C | 2° C |
| Mechanical Properties | | | |
| 23 hr cure | | | |
| Tensile, PSI | 734 | 238 | — |
| Elongation % | 147 | 155 | — |
| 47 hr cure | | | |
| Tensile, PSI | 758 | 380 | 19 |
| Elongation, % | 133 | 139 | 441 |
| 115 hr cure | | | |
| Tensile, PSI | — | — | 112 |
| Elongation, % | — | — | 151 |

EXAMPLE XX

The high specificity of the active chromium III-tricarboxylate catalysts for promoting the oxirane/carboxylic acid reaction is illustrated in this example, as well as their general applicability in this reaction.

The following compositions were prepared di- and polyepoxides reacted with monofunctional carboxylic acids with active chromium III-tri-2-ethylhexanoate (COT) and inactive chromium III-tri-2-ethylhexanoate trihydrate (COT $3H_2O$)*, as well as with no catalyst at all. The epoxides used were the diglycidyl ether of bisphenol-A (A), the polyglycidyl ether of a phenol-formaldehyde polymer (B) and vinyl cyclohexane dioxide, (C), the acids used were acetic acid, (D) acrylic acid, (E) and 2-ethylhexanoic acid. (F)

*Used in only one case for purposes of comparison.

See Table Below

TABLE III

REACTIONS OF POLYEPOXIDES WITH CARBOXYLIC ACIDS at a Temperature of 22°C

| | Reaction of A + E | | | | Reaction of B + D | | | | Reaction of C + F | | | | | |
|---|---|---|---|---|---|---|---|---|---|---|---|---|---|---|
| | A | | F | | B | | D | | C | | | F | | |
| | Uncat. | COT | Uncat. | COT | Uncat. | COT | Uncat. | COT | Uncat. | COT | COT. 3H$_2$O | Uncat. | COT | COT. 3H$_2$O |
| Initial Meg/g | 4.054 | 4.054 | 3.160 | 3.160 | 4.180 | 4.180 | 3.836 | 3.836 | 4.787 | 4.787 | 4.787 | 4.459 | 4.459 | 4.459 |
| 20 hr., Meq/g | 3.990 | 1.365 | 3.161 | 0.636 | 4.133 | 2.095 | 3.836 | 1.980 | 4.286 | 0.633 | 3.675 | 4.296 | 0.602 | 3.912 |
| 20 hr., % reacted | 1.6 | 66.3* | 0 | 79.9 | 1.0 | 49.9* | 0 | 47.0 | 10.5 | 86.8* | 23.2 | 3.6 | 86.5 | 12.3 |
| 40 hr., Meq/g | 3.974 | 0.740 | 3.244 | 0 | 4.069 | 1.351 | 3.672 | 1.362 | 4.008 | 0.361 | — | 4.125 | 0.323 | — |
| 40 hr., % reacted | 2.0 | 81.7* | 0 | 100 | 2.6 | 67.7* | 4.2 | 64.5 | 16.3 | 92.4* | <40 | 7.5 | 86.5 | <30 |

| Ratio of epoxy/acid consumed in a 40 hour period | Ratio |
|---|---|
| A + E Uncatalyzed | Little or no reaction |
| A + E COT catalyzed | 1.07 |
| B + D Uncatalyzed | Little or no reaction |
| B + D COT catalyzed | 1.14 |
| C + F Uncatalyzed | 2.3 |
| C + F COT catalyzed | 1.07 |
| C + F COT . 3H$_2$O catalyzed (inactive) | 2.03 |

*Since the epoxide was present in an excess amount, the extent of reaction of epoxide is best judged by the amount of acid consumed. Only less than 15% of the total epoxide present is used up in a homopolymerization reaction, as is shown by the stoichiometric ratios of material consumed with the invention catalyst as oposed to the presence of no catalyst or inactive chromium compound.

COT = active chromium octate

The products prepared in accordance with this invention are useful in films for wire and cable wrap, motor insulation, surface coatings, lacquers, textile fibers, adhesives, molding resins, fiber glass laminates for use in aircraft parts, honeycombs electrical conductive films when properly coated, and foams, as well as for intermediates in the production of other chemical compounds.

Low molecular weight monomeric compounds are useful as diluents, plasticizers, polymeric intermediates and lubricants.

It should also be noted that one or more than one compound of each class of epoxides may be reacted with one or more than one acid. Thus a monomeric monofunctional oxirane could be used in conjunction with a polyfunctional polymeric epoxide, for example if such is desired. Similarly mono and poly acids can be utilized together.

Furthermore, the curable mixtures of the invention may be mixed at any stage prior to the completion of the degree of reaction possible as limited by the amount of one of the reactants, with fillers, plasticizers, pigments, dyestuffs, flame-inhibitors, mould lubricants or the like. Suitable extenders and fillers are, for example, asphalt, bitumen, glass fibers, mica, quartz meal, cellulose, kaolin, ground dolomite, colloidal silica having a large specific surface (Aerosil) or metal powders, such as aluminum powder.

Curable mixtures may be used in the unfilled or filled state, if desired in the form of solutions or emulsions, as laminating resins, pains, lacquers, dipping resins, molding compositions, coating compositions, pore fillers, floor coverings, potting and insulating compounds for the electrical industry, adhesives and the like, and also in the manufacture of such products.

It is to be further understood that while the oxirane compounds can be reacted with the acids throughout the range of from about 0° C to 250° C, there are certain situations wherein a particular temperature range should be utilized. For instance, if one of the reactants contains heat sensitive groups such as carbon to carbon double bonds, temperatures over about 50° C should be avoided. The desired rate of catalysis can also be achieved by the adjustment of catalyst level as well as by an increase in temperature.

Operating temperatures are determined by the temperature necessary to maintain mobility of the reactive constituents. Solvents help to maintain mobility and thereby allow low temperature reactions to be carried out.

Rubbery end products are preferably prepared at temperatures below 75° C, though elevated temperatures give rise to equally satisfactory products with respect to certain physical properties.

Since certain changes may be made in the above compositions and processes without departing from the scope of the invention herein involved, it is intended that all matter contained in the above description shall be interpreted as illustrative and not in a limiting sense.

We claim:

1. A method of forming as ester linkage which comprises reacting an organic carboxylic acid with an organic oxirane compound in the presence of an effective catalytic amount of soluble chromium III carboxylate of the formula:

where $OOCR^a$ is a carboxylate group containing at least 4 carbon atoms, said catalyst being the reaction product of a hydrated Cr III tricarboxylate heated in an excess of organic acid to a temperature above 140° C and said reaction product having the following characteristics:
1. emerald green in color;
2. slightly soluble in hexane but fully soluble in acetone;
3. melts slightly above room temperature;
4. does not exhibit a water absorption peak at 2750 m$\mu$ in the near infrared
5. at least 90% of the carboxylate carbonyl absorption is at 1615 cm$^{-1}$ and not at 1540 cm$^{-1}$.

2. A method according to claim 1 in which $OOCR^a$ is selected from butyrate, pentanoate, hexanoate, 2-ethyl, hexanoate, decanoate, oleate, stearate, toluate, cresylate, benzoate, alkyl benzoate, alkoxybenzoate, and napthenate.

3. A method according to claim 2 in which $OOCR^a$ is 2-ethyl hexanoate.

4. A method according to claim 1 in which the organic oxirane compound is of the formula:

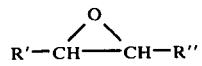

where R' and R'' are individually selected from the group consisting of hydrogen and alkyl of 1 to 20 carbon atoms.

5. The method of claim 1 wherein the esterification reaction is carried out at about ambient temperature.

6. The method of claim 1 wherein the chromium III carboxylate is present in an amount of from 0.1% to about 10% by weight of reactants.

7. The method of claim 4 wherein the oxirane compound is selected from the group consisting of ethylene oxide, propylene oxide, 1,2-butylene oxide and 2,3-butylene oxide.

8. The method of claim 1 wherein the organic carboxylic acid contains one (—COOH) group and the oxirane is mono functional.

9. The method of claim 8 wherein the organic carboxylic acid is selected from the group consisting of 2-ethylhexanoic, adipic, acrylic, acetic, azelaic, oxalic, cyclohexanetricarboxylic, trimesic, sebacic, terephthalic acids and polyacrylic acids.

10. The method of claim 1 wherein a stoichiometric amount of acid is reacted with a stoichiometric amount of oxirane.

11. The method of claim 1 wherein the oxirane compound is selected from the group consisting of a glycidyl ether of a mono-functional alcohol, a glycidyl ether of a monofunctional phenol, and a glycidyl ether of a monofunctional organic acid.

12. The method of claim 1 wherein the oxirane compound contains at least two oxirane groups.

13. The method of claim 1 wherein the oxirane compound is a polyepoxide resin.

14. The method of claim 1 wherein the organic carboxylic acid is a difunctional or polyfunctional.

15. The method of claim 1 wherein the organic carboxylic acid contains at least two carboxyl groups.

* * * * *

UNITED STATES PATENT AND TRADEMARK OFFICE
CERTIFICATE OF CORRECTION

PATENT NO. : 4,017,429
DATED : April 12, 1977
INVENTOR(S) : Roger B. Steele and Arthur Katzakian, Jr.

It is certified that error appears in the above-identified patent and that said Letters Patent are hereby corrected as shown below:

Column 1, line 13, correct -- and --
Column 3, line 52, change "processing" to -- possessing --
Column 10, line 12, change ",," to -- , --
Columns 9 and 10, Table II, last line, change "10.03" to -- 10.18--
Columns 9 and 10, line 3, after Table II, change "percent of Wt%
  $H_2O$ based upon molecular weight" to -- percentages do not represent the weight percent of water present on the molecule. --
Column 11, line 26, correct -- compounds --
Column 11, line 38, change "th" to -- the --
Column 13, line 60, correct -- allowed --
Column 13, lines 66-67, change "elements" to -- elemental --
Column 14, line 19, change "(3.6, g" to -- (3.6g, --
Column 15, line 63, change "has" to -- was --
Column 16, in the table, 1st column, insert the following heading
  -- Reaction Time Hours --
Column 16, line 23, after "acetone", add -- solution --
Column 16, line 46, correct -- Ethylhexanoate --
Column 16, line 50, after "titrimeter.", add -- Results: --
Column 16, line 68, correct -- novel --
Column 17, line 22, change "acceleration" to -- accelerating --
Column 17, line 26, change "ERL-4421" to -- ERL-4221 --
Column 18, line 21, after "prepared", insert -- from --
Columns 17 and 18, Table III, 1st Column, 2nd line, change "Meg/g"
  to -- Meq/g --

UNITED STATES PATENT OFFICE
CERTIFICATE OF CORRECTION

Patent No. 4,017,429  Dated April 12, 1977

Inventor(s) Roger B. Steele and Arthur Katzakian, Jr.

It is certified that error appears in the above-identified patent and that said Letters Patent are hereby corrected as shown below:

Columns 17 & 18, line 2, after Table III, correct --opposed --
line 4, after Table III, correct --octoate --

Signed and Sealed this

Sixth Day of December 1977

[SEAL]

Attest:

RUTH C. MASON  
*Attesting Officer*

LUTRELLE F. PARKER  
*Acting Commissioner of Patents and Trademarks*